United States Patent [19]

Evans et al.

[11] Patent Number: 4,610,992

[45] Date of Patent: Sep. 9, 1986

[54] TRANS-4-(2-THIAOXO-1-PYRROLIDINYL OR PIPERIDINYL)-2H-BENZO[B]PYRAN-3-OL DERIVATIVES USEFUL IN TREATING HYPERTENSION

[75] Inventors: John M. Evans, Roydon; Robin E. Buckingham, Welwyn Garden City; Kenneth Willcocks, Harlow, all of England

[73] Assignee: Beecham Group p.l.c., England

[21] Appl. No.: 592,115

[22] Filed: Mar. 22, 1984

[30] Foreign Application Priority Data

Mar. 24, 1983 [GB] United Kingdom ............... 8308064

[51] Int. Cl.⁴ .................. A61K 31/445; A61K 31/40; C07D 405/04
[52] U.S. Cl. .................................. 514/320; 514/278; 514/409; 514/422; 548/407; 548/525; 546/15; 546/196
[58] Field of Search ............... 548/525, 407; 546/196, 546/15; 514/278, 320, 409, 422

[56] References Cited

U.S. PATENT DOCUMENTS

| | | | |
|---|---|---|---|
| 4,363,811 | 12/1982 | Evans et al. | 548/525 |
| 4,366,163 | 12/1982 | Evans et al. | 546/196 |
| 4,446,113 | 5/1984 | Evans et al. | 424/267 |
| 4,510,152 | 4/1985 | Faruk | 546/196 X |

FOREIGN PATENT DOCUMENTS 46652  3/1982  European Pat. Off. ........... 549/399

OTHER PUBLICATIONS

Lap et al., Aust. J. Chem., 1979, 32 pp. 619-636.
Burger, ed., *Medicinal Chemistry,* Third Edition Part I, Wiley-Interscience, N.Y., (1970), pp. 72-74.

*Primary Examiner*—Donald G. Daus
*Assistant Examiner*—William A. Teoli, Jr.
*Attorney, Agent, or Firm*—Jacobs & Jacobs

[57] ABSTRACT

A compound of formula (I):

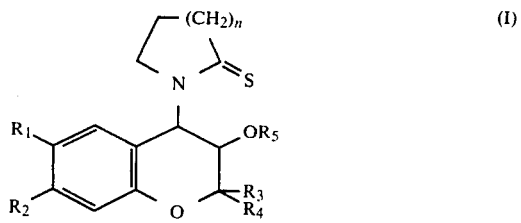

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, 1-mercapto-$C_{2-7}$ alkyl, formyl or aminosulphinyl, aminosulphonyl or aminocarbonyl, the amino moiety being optionally substituted by one or two $C_{1-6}$ alkyl groups, or $C_{1-6}$ alkysulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH₂, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl; one of $R_3$ and $R_4$ is hydrogen or $C_{1-4}$ alkyl and the other is $C_{1-4}$ alkyl or $R_3$ and $R_4$ together are $C_{2-5}$ polymethylene.

$R_5$ is hydrogen, $C_{1-3}$ alkyl or $C_{1-8}$ acyl; and n is 1 or 2; the thiolactam group being trans to the $OR_5$ group; or, when one or the other of $R_1$ and $R_2$ is an amino or an amino-containing group capable of forming an acid addition salt, a pharmaceutically acceptable salt thereof, having useful pharmacological activity, a process for preparing them, pharmaceutical compositions containing them, and their use in the treatment of mammals.

9 Claims, No Drawings

TRANS-4-(2-THIAOXO-1-PYRROLIDINYL OR PIPERIDINYL)-2H-BENZO[b]PYRAN-3-OL DERIVATIVES USEFUL IN TREATING HYPERTENSION

ACTIVE COMPOUNDS

The present invention relates to novel compounds having pharmacological activity, to a process for preparing them, to pharmaceutical compositions containing them, and to their use in the treatment of mammals.

U.S. Pat. Nos. 4,110,347 and 4,251,537, and European Published Applications Nos. 9912, 28449 and 28064 describe 3,4-dihydrobenzopyrans having hypotensive activity.

A further class of 3,4-dihydrobenzopyrans have now been discovered which are characterised by the presence of a thiaoxo group in a nitrogen-containing ring which substitutes the 3,4-dihydrobenzopyran in the 4-position. Such compounds have been found to have blood pressure lowering activity.

Accordingly, the present invention provides a compound of formula (I):

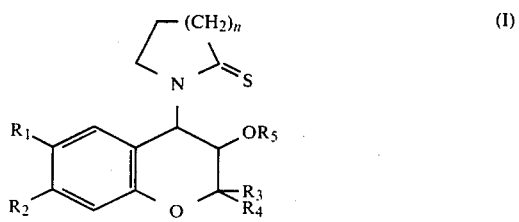

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto-$C_{2-7}$ alkyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or $-C(C_{1-6}$ alkyl)NOH or $-C(C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl;
one of $R_3$ and $R_4$ is hydrogen or $C_{1-4}$ alkyl and the other is $C_{1-4}$ alkyl or $R_3$ and $R_4$ together $C_{2-5}$ polymethylene;
$R_5$ is hydrogen, $C_{1-3}$ alkyl or $C_{1-8}$ acyl;
n is 1 or 2; the thiolactam group being trans to the OR$_5$ group; or, when one of $R_1$ and $R_2$ is an amino or an amino-containing group capable of forming an acid addition salt, a pharmaceutically acceptable salt thereof.

When one of $R_1$ and $R_2$ is hydrogen, the other is preferably selected from the class of $C_{1-6}$ alkylcarbonyl, $C_{1-6}$ alkoxycarbonyl, nitro and cyano. In particular, when one of $R_1$ and $R_2$ is hydrogen, the other is preferably nitro, cyano, or $C_{1-6}$ alkylcarbonyl such as acetyl.

When one of $R_1$ and $R_2$ is hydrogen, it is preferred that $R_2$ is hydrogen.

When one of $R_1$ and $R_2$ is nitro, cyano or $C_{1-3}$ alkylcarbonyl and the other is not hydrogen, the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are each alkyl having from 1 to 4 carbon atoms. In particular they are each methyl or ethyl, preferably both methyl.

When $R_5$ is $C_{1-3}$ alkyl, preferred examples thereof include methyl, ethyl and n-propyl, of which methyl is most preferred. When $R_5$ is $C_{1-8}$ acyl, a preferred class is unsubstituted carboxylic acyl, such as aliphatic acyl or benzoyl. $R_5$ is preferably hydrogen or $C_{1-8}$ acyl, in particular hydrogen.

It is preferred that the compounds of formula (I) are in substantially pure form, or in crystalline form.

The compounds of formula (I) have asymmetric centres and therefore exist in optically active forms. The present invention extends to all such forms individually and to mixtures of them.

Particularly preferred examples of a compound of formula (I) include
6-cyano-3,4-dihydro-2,2-dimethyl-trans-4-(2-thiaoxo-1-pyrrolidinyl)-2H-benzo[b]pyran-3-ol;
6-acetyl-3,4-dihydro-2,2-dimethyl-trans-4-(2-thiaoxo-1-pyrrolidinyl)-2H-benzo[b]pyran-3-ol;
6-acetyl-3,4-dihydro-2,2-dimethyl-trans-4-(2-thiaoxo-1-piperidinyl)-2H-benzo[b]pyran-3-ol;
6-cyano-3,4-dihydro-2,2-dimethyl-trans-4-(2-thiaoxo-1-piperidinyl)-2H-benzo[b]pyran-3-ol;
6-nitro-3,4-dihydro-2,2-dimethyl-trans-4-(2-thiaoxo-1-pyrrolidinyl)-2H-benzo[b]pyran-3-ol; and
6-nitro-3,4-dihydro-2,2-dimethyl-trans-4-(2-thiaoxo-1-piperidinyl)-2H-benzo[b]pyran-3-ol.

The present invention also provides a process for the preparation of a compound of formula (I), which comprises the thiation of a compound of formula (II);

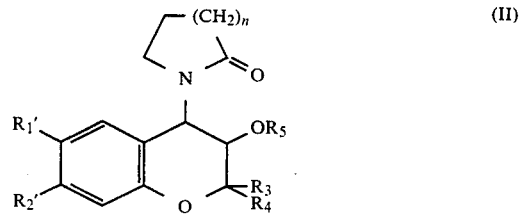

wherein $R_1'$ and $R_2'$ are $R_1$ and $R_2$ respectively or $R_1'$ or $R_2'$ is a group or atom convertible into $R_1$ or $R_2$ respectively, $R_1$ and $R_2$ being as defined hereinbefore, and $R_3$ to $R_5$ and n are as defined hereinbefore, the lactam group being trans to the OR$_5$ group; in the case when $R_1'$ or $R_2'$ is a group or atom convertible into $R_1$ or $R_2$ respectively, converting the group or atom into $R_1$ or $R_2$; optionally converting $R_1$ or $R_2$ in the compound of formula (I) so obtained into another $R_1$ or $R_2$ as defined hereinbefore; optionally converting $R_5$ in the compound of (I) so obtained into another $R_5$, as defined hereinbefore; and, when one of $R_1$ and $R_2$ in the compound of formula (I) so obtained is an amino or an amino-containing group capable of forming an acid addition salt, optionally forming a pharmaceutically acceptable salt thereof.

The thiation reaction is preferably carried out with conventional thiation agents, such as hydrogen sulphide, phosphorous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

If the process of the present invention is to be used to prepare a compound of formula (I), wherein $R_1$ or $R_2$ is a carbonyl-containing group, then it is preferred to use the corresponding compound of formula (II), wherein $R_1'$ or $R_2'$ is a protected carbonyl-containing group, in the thiation reaction, and afterwards to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Similarly, if the process of the present invention is to be used to prepare a compound of formula (I), wherein $R_5$ is hydrogen, it may be desirable to use for $R_5$ in the corresponding compound of formula (II) a $C_{1-8}$ acyl group, such as a tosyl or mesyl group, and then, after the thiation reaction has been carried out, to remove the $C_{1-8}$ acyl group. In this way, the use of, for example, phosphorous pentasulphide will not give rise to the thiation of the hydroxy group. If, however, the greatly preferred Lawesson's reagent is used, then there is no need to protect the hydroxy group since little, if any, hydroxy thiation takes place.

Conversion of a group or atom $R_1'$ or $R_2'$ in the compound resulting from the thiation reaction to $R_1$ or $R_2$ are generally known reactions. In addition to the conversion of $R_1'$ or $R_2'$ groups containing protected carbonyl to $R_1$ or $R_2$ groups containing carbonyl, examples of such conversions include the following; A hydrogen atom may be replaced by a nitro group by nitrating in a known manner the compound wherein one of $R_1'$ and $R_2'$ is hydrogen and the other is acetamido, followed by hydrolysing the compound, converting the resulting amine into a diazonium salt, and finally decomposing it, leaving a compound of formula (I), wherein one of $R_1$ and $R_2$ is hydrogen and the other is nitro.

The known methods of $R_1'$ and $R_2'$ interconversion with $R_1$ and $R_2$ (lying within the definition of $R_1'$ and $R_2'$) are applicable to all $R_1'$ and $R_2'$ interconversions hereinafter.

Apart from the conversion of a protected carbonyl-containing group into a carbonyl-containing group it is preferred that any other conversion of a group or atom into $R_1$ or $R_2$ is carried out at an earlier stage.

Examples of optional conversions of $R_1$ or $R_2$ in a compound of formula (I) into another $R_1$ or $R_2$, as defined hereinbefore, are generally known in the art of aromatic chemistry. For example, an α-hydroxyethyl group may be converted into acetyl by oxidation, a chloro atom may be converted into an amino group by amination, an amino group may be converted into amino substituted by one or two $C_{1-6}$ alkyl or by $C_{2-7}$ alkanoyl, or an hydrogen atom may be converted into a nitro group by nitration.

Example of optional conversions of $R_5$ in a compound of formula (I) into another $R_5$ are generally known in the art. For example, when $R_5$ is hydrogen, the hydroxy group may be alkylated using an alkyl iodide in an inert solvent, such as toluene, in the presence of a base, such as potassium hydroxide. Alternatively, the hydroxy group may be acylated using a carboxylic acid or a derivative thereof, such as the chloride or anhydride, in a non-hydroxylic solvent in the presence of a condensation promoting agent, such as dicyclohexylcarbodiimide. Such methods are applicable to all such $R_5$ interconversions hereinafter.

When one of $R_1$ and $R_2$ in the compound of formula (I) so obtained is an amino or an amino-containing group, the optional formation of a pharmaceutically acceptable salt thereof may be carried out in accordance with conventional procedures.

The compound of formula (II) may be prepared by cyclising a compound of formula (III), or metal salt thereof:

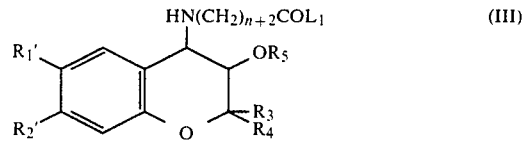

wherein $R_1'$, $R_2'$, $R_3$ to $R_5$ and n are as defined hereinbefore, the substituted amino group is trans to the $OR_5$ group, and $L_1$ is a leaving group.

Groups $R_1'$, $R_2'$ and $R_5$ in the resultant compound of formula (II) may be converted to other groups $R_1'$, $R_2'$ and $R_5$ as described for such groups in the compound of formula (II).

The leaving group ($L_1$) is a group that is displaceable by a secondary amino nucleophile. Preferred examples of such groups include hydroxy and, in particular, $C_{1-4}$ alkoxy, such as ethoxy.

The cyclisation is normally carried out by heating the compound of formula (III) under reflux in an inert solvent, such as xylene or toluene.

When a metal salt of formula (III) is used, the sodium salt is preferred. However, it is even more preferred not to use a metal salt at all, especially as any elimination side reactions are thereby avoided.

A compound of formula (III) may be prepared by reacting a compound of formula (IV):

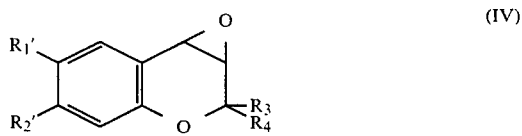

wherein $R_1'$ and $R_2'$ and $R_3$ and $R_4$ are as defined hereinbefore, with a compound of formula (V):

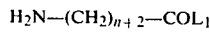  (V)

wherein n and L₁ are as defined hereinbefore; and optionally converting the R₅ hydrogen atom in the resulting compound of formula (III) to other R₅ as hereinbefore defined.

The reaction is normally carried out in a solvent at low, medium or high temperature. The solvent may be an alcohol, such as methanol or ethanol.

When L₁ is hydroxy the reaction proceeds well if carried out in refluxing ethanol in the presence of aqueous sodium carbonate. When L₁ is $C_{1-4}$ alkoxy, the reaction is preferably carried out in the presence of sodium hydroxide in ethanol.

Under some conditions, the compound of formula (III) may spontaneously cyclise to form a compound of formula (II).

A compound of formula (IV) may be prepared, preferably in situ, by reacting a compound of formula (VI):

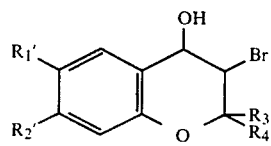  (VI)

wherein $R_1'$, $R_2'$, $R_3$ and $R_4$ are as defined hereinbefore and the hydroxy group is trans to the bromo atom, with a base, such as potassium hydroxide, in ether or aqueous dioxan.

Alternatively, a compound of formula (III) may be prepared by reacting a compound of formula (VII):

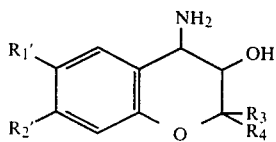  (VII)

wherein $R_1'$, $R_2'$, $R_3$ and $R_4$ are as defined hereinbefore, and the amino group is trans to the hydroxy group, with a compound of formula (VIII):

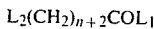  (VIII)

wherein n and L₁ are as defined hereinbefore and L₂ is a leaving group; and optionally converting the R₅ hydrogen atom in the resulting compound of formula (III) to other R₅ as hereinbefore defined.

The leaving group (L₂) is a group that is displaceable by a primary amino nucleophile. Preferred examples of such groups includes halo, such as chloro and bromo.

A compound of formula (VII) may be prepared by a reaction of a compound of formula (IV) with ethanolic ammonium hydroxide solution. Alternatively, it may be prepared by reduction with zinc and hydrochloric acid of a compound of formula (IX):

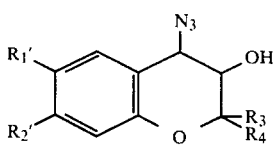  (IX)

wherein $R_1'$, $R_2'$, $R_3$ and $R_4$ are as defined hereinbefore and wherein the azide group is trans to the hydroxy group.

A compound of formula (IX) may in turn be prepared from a compound of formula (IV) by reaction with sodium azide in the presence of boric acid in for example dimethylformamide.

Alternatively, a compound of formula (II) may be prepared by oxidising a compound of formula (X), or a metal salt thereof:

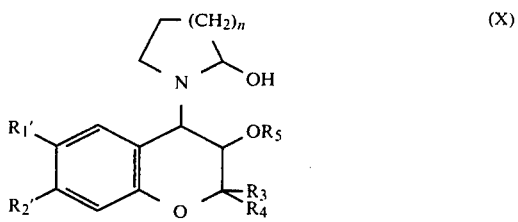  (X)

wherein $R_1'$, $R_2'$, $R_3$, to $R_5$ and n are as defined hereinbefore, and wherein the cyclic aminol group is trans to the OR₅ group; and optionally converting $R_1'$, $R_2'$ or R₅ in the resultant compound of formula (II) to other $R_1'$, $R_2'$ or R₅ as hereinbefore defined.

The oxidation is preferably carried out in a solvent such as aqueous methanol with a metal periodate such as potassium periodate.

A compound of formula (X) may be prepared by cyclising in the presence of an acid a compound of formula (XI):

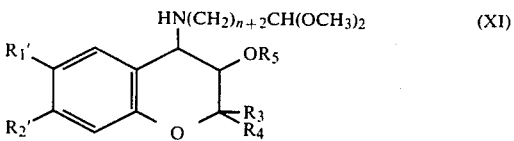  (XI)

wherein $R_1'$, $R_2'$, $R_3$ to $R_5$ and n are as defined hereinbefore and wherein the substituted amino group is trans to the OR₅ group.

A compound of formula (XI) may in turn be prepared by reacting a compound of formula (IV) with a compound of formula (XII):

  (XII)

wherein n is as defined hereinbefore.

As a further alternative, a compound of formula (II) may be prepared by reacting a compound of formula (IV) with an anion of formula (XII):

  (XIII)

wherein n is as defined hereinbefore; and optionally converting $R_1'$, $R_2'$ or R₅ in the resultant compound of formula (II) to other $R_1'$, $R_2'$ or R₅ as hereinbefore defined.

The reaction is preferably carried out in a solvent such as dimethylsulphoxide in the presence of a base, such as sodium hydride.

A compound of formula (IV) may be prepared in situ from the corresponding compound of formula (VI). In such circumstances, it is advantageous not to add the lactam of formula (XIII) until sufficient time has elapsed for the epoxide of formula (IV) to be produced.

As a yet further alternative, a compound of formula (II) may be prepared by cyclising a compound a formula (XIV):

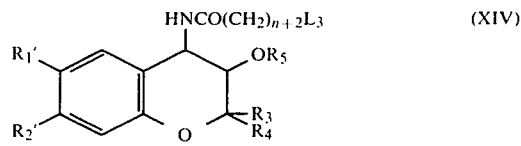

(XIV)

wherein $R_1'$, $R_2'$, $R_3$ to $R_5$ and n are as defined hereinbefore and $L_3$ is a leaving group, and wherein the substituted amino group is trans to the $OR_5$ group; and optionally converting $R_1'$, $R_2'$ or $R_5$ in the resultant compound of formula (II) to other $R_1'$, $R_2'$ or $R_5$ as hereinbefore defined.

The leaving group ($L_3$) is a group that is displaceable by a secondary amino nucleophile adjacent a carbonyl function. A preferred example is chloro.

The cyclisation reaction is preferably carried out in a solvent such as dimethylformamide in the presence of a base, such as sodium hydride.

A compound of formula (XIV) may be prepared by reacting a compound of formula (VII) with a compound of formula (XV):

$$L_3(CH_2)_{n+2}COL_4 \quad (XV)$$

wherein $L_3$ and n are as defined hereinbefore and $L_4$ is a leaving group.

The leaving group ($L_4$) is a group that, when adjacent to a carbonyl function, is displaceable by a primary amino nucleophile.

The reaction is preferably carried out in a solvent, such as chloroform or methylene chloride, in the presence of aqueous base, such as aqueous sodium hydroxide.

In the reactions with the epoxide of formula (IV), the trans isomer is specifically formed.

Compounds of formula (VI) are known and may be prepared in accordance with any appropriate known process, for example, by the process described in the aforementioned U.S. patents and European patent publications. Schematically, such process can be depicted thus:

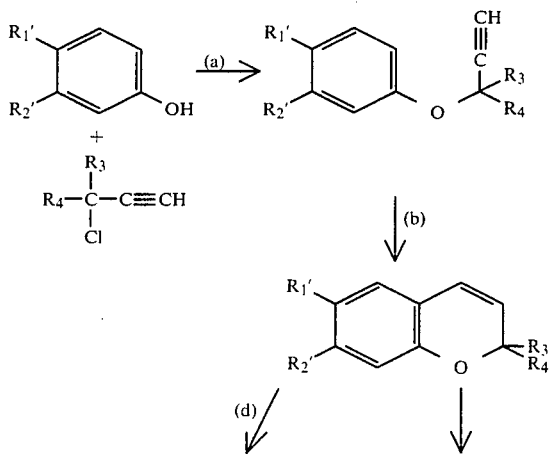

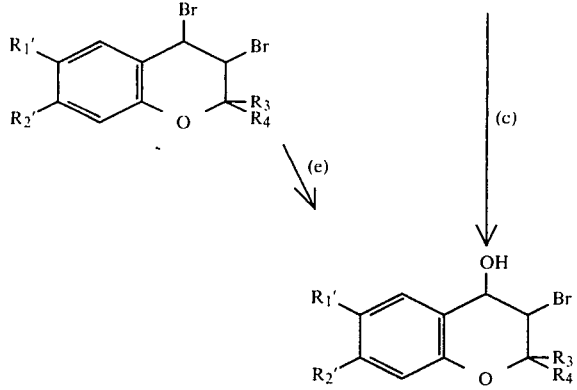

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

As mentioned previously, the compounds of formula (I) exist in optically active forms, and the processes of the present invention produce mixtures of such forms. The individual isomers may be separated one from another conventionally.

It is preferred that the compounds of formula (I) are isolated in substantially pure form, or in crystalline form.

As mentioned previously, the compounds of formula (I) have been found to have blood-pressure lowering activity. They are therefore useful in the treatment of hypertension.

The present invention accordingly provides a pharmaceutical composition which comprises a compound of formula (I) or a pharmaceutically acceptable salt thereof and a pharmaceutically acceptable carrier. In particular, the present invention provides an anti-hypertensive pharmaceutical composition which comprises an anti-hypertensive amount of a compound of formula (I) or a pharmaceutically acceptable salt thereof and a pharmaceutically acceptable carrier.

The compositions are preferably adapted for oral administration. However, they may be adapted for other modes of administration, for example parenteral administration for patients suffering from heart failure.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose;

or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the suffer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The present invention further provides a compound of formula (I) or a pharmaceutically acceptable salt thereof for use in the treatment or prophylaxis of hypertension.

The following descriptions relate to the preparation of intermediates and the following examples relate to the preparation of a compound of formula (I).

All temperatures therein are in °C.

DESCRIPTION 1

6-Cyano-3,4-dihydro-2,2-dimethyl-3,4-epoxy-2H-benzo[b]-pyran

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperaure for 1.5 hours under nitrogen, After distillation of the solvent the fraction boiling at 110°–114°/0.02 mmHg (16.57 g) was collected, which on standing formed a low melting solid, having an IR absorption at 2230 cm$^{-1}$. (See M. Harfenist and E. Thom, *J. Org. Chem.*, 841 (1972) who quote m.p. 36°–37°).

Addition to this 6-cyanochromene (16.50 g) dissolved in dimethyl sulphoxide (150 ml) containing water (3.24 ml) of N-bromosuccinimide (31.90 g) with vigorous stirring and cooling, followed by dilution with water and extraction via ethyl acetate gave a mixture which was boiled in acetone (300 ml) and water (100 ml) for 5 hours to hydrolyse the small amount of 3,4-dibromide present. Evaporation of solvents gave 6-cyano-trans-3-bromo-3,4-dihydro-2,2-dimethyl-2H-benzo[b]pyran-4-ol as white crystals (24.37 g). A small sample had m.p. 128°–128.5° from 60°–80° petroleum ether, nmr (CDCl$_3$) 1.43 (3H), 1.62 (3H), 7.48 (1H, exchangeable), 4.07 (1H, d, J=9), 4.87 (1H, d, J=9), 6.80 (1H, d, J=8), 7.43 (1H, q, J=8, 2), 7.78 (1H, d, J=2). Analysis calculated for C$_{12}$H$_{12}$NO$_2$Br:C, 51.07; H, 4.26; N, 4.96; Br, 28.37. Found: C, 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 6-cyano-3,4-dihydro-2,2-dimethyl-3,4-epoxy-2H-benzo[b]pyran (16.02 g) as a gum, having an absorption at 2230 cm$^{-1}$ in the IR and Nmr (CCl$_4$) 1.26 (3H), 1.54 (3H), 3.40 and 3.80 (each 1H, d, J=4), 6.77 (1H, d, J=8), 7.43 (1H, q, J=8, 2), 7.58 (1H, d, J=2).

DESCRIPTION 2

6-Cyano-3,4-dihydro-2,2-dimethyl-trans-4-amino-2H-benzo[b]pyran-3-ol

The title compound was prepared by stirring 6-cyano-3,4-dihydro-2,2-dimethyl-3,4-epoxy-2H-benzo[b]pyran in ethanolic ammonium hydroxide solution at room temperature until thin layer chromatography showed consumption of the starting epoxide.

DESCRIPTION 3

6-Cyano-3,4-dihydro-2,2-dimethyl-trans-4-(1-oxo-4-chlorobutylamino)-2H-benzo[b]pyran-3-ol The amino chromanol (1.40 g), as obtained in Description 2, was stirred in chloroform (20 ml) and water (10 ml) containing sodium hydroxide pellets (0.26 g) at room temperature. 4-Chlorobutyryl chloride (0.72 ml) was added and the reaction stirred vigorously for 0.5 hours. Separation of the layers and washing the organic layer with water, then brine, drying over magnesium sulphate, filtration and evaporation gave the title compound as a pale yellow solid.

DESCRIPTION 4

6-Cyano-3,4-dihydro-2,2-dimethyl-trans-4-(4,4-diethoxybutylamino)-2H-benzo[b]pyran-3-ol 6-Cyano-3,4-dihydro-2,2-dimethyl-3,4-epoxy-2H-benzo[b]pyran (200 mg) and 4-aminobutyraldehyde diethylacetal (200 mg) were heated to 100° C. for 1.5 hours, a clear yellow solution forming during this time. After cooling, dilution with ether, and washing successively with water and brine, drying over sodium sulphate and evaporation, the aminoacetal was obtained as a pale yellow oil (291 mg).

DESCRIPTION 5

6-Cyano-3,4-dihydro-2,2-dimethyl-trans-4-(2-hydroxy-1-pyrrolidinyl)-2H-benzo[b]pyran-3-ol The oily acetal, as obtained in Description 4, was dissolved in dioxan (2 ml) and treated with 2.5M HCl (1 ml). After 30 minutes the reaction was diluted with ether and neutralised with sodium carbonate solution.

The two phases were separated, the aqueous layer further extracted with ether and the combined extracts washed with water and brine and dried over sodium sulphate. The organic phase was filtered and applied to Kieselgel 60 (10 g) and diluted with ethyl acetate-heptane-triethylamine (10:20:2). Three fractions were obtained (total 128 g) containing the title compound. TLC (silica gel; ethyl acetate-heptane-triethylamine (10:20:2) showed the presence of varying amounts of the two positional isomers in each fraction.

IR (KBr disc) 3450, 2230 cm$^{-1}$ for all three fractions.

Mass spectrum (Isobutane and ammonium C.I.) showed m/z 271 (MH$^+$—H$_2$O) for all three fractions.

DESCRIPTION 6

6-Cyano-3,4-dihydro-2,2-dimethyl-trans-4-(2-oxo-1-pyrrolidinyl)-2H-benzo-[b]-pyran-3-ol 6-Cyano-3,4-dihydro-2,2-dimethyl-3,4-epoxy-2H-benzo-[b]-pyran (0.50 g), as obtained in Description 1, 4-aminobutyric acid (1.25 g) and sodium bicarbonate (1.00 g) were refluxed in ethanol (15 cc) and distilled water (2.5 cc) for 10 hours. The reaction was filtered and evaporated and the residue chromatographed on 25 g Kieselgel 60. Elution with MeOH-chloroform (1:3) gave 132 mg of the most polar product. This was refluxed in toluene (10 cc) for 2 hours, cooled and the solvent evaporated. The residue was chromatographed on 5 g Kieselgel 60 and eluted with MeOH-chloroform (1:3) to give the title compound as a white solid (90 mg), m.p. 230°–231°.

IR (KBr disc): 3260, 2220, 1651 cm$^{-1}$;

NMR (CDCl$_3$):

1.28 (3H);
1.55 (3H);
2.11 (2H, m);
2.57 (2H, m); 3.22 (3H, 1 exchangeable H, broad m);
3.64 (1H, d, J=10);
5.26 (1H, d, J=10);
6.87 (1H, d, J=9);
7.24 (1H, narrow m);
7.45 (1H, q, J=9, 2);

Analysis calculated for C$_{16}$H$_{18}$N$_2$O$_3$: C, 67.12; H, 6.34; N, 9.78%. Found C, 66.83; H, 6.17; N, 9.50%.

DESCRIPTION 7

6-Cyano-3,4-dihydro-2,2-dimethyl-trans-4-(2-oxo-1-pyrrolidinyl)-2H-benzo-[b]-pyran-3-ol 6-Cyano-3,4-dihydro-2,2-dimethyl-3,4-epoxy-2H-benzo-[b]-pyran (1.00 g), as obtained in Description 1, ethyl-4-aminobutyrate hydrochloride (0.84 g), ethanol (50 ml) and sodium hydroxide pellets (0.20 g) were stirred at room temperature for 8 days, then at 40< for 3 hours. After cooling and evaporation the residue was taken up in ethyl acetate and filtered. Evaporation of the filtrate gve a gum (1.46 g) which was chromatographed using a chromatotron (2 mm silica gel HF$_{254}$ plate; 2 runs; solvent flow rate 6 ml/min.). Elution with 2% methanol-chloroform mixture gave starting epoxide (0.23 g) followed by a more polar ester fraction (0.64 g), and a mixture (0.15 g) which on further chromatography under identical conditions gave 6-cyano-3,4-dihydro-2,2-dimethyl-trans-4-(2-oxo-1-pyrrolidinyl)-2H-benzo[b]pyran-3-ol having an identical NMR spectrum to that obtained in Description 6.

A portion of the ester fraction (150 mg) was dissolved in ether containing a little ethanol and treated with anhydrous ethanolic HCl. The precipitate was collected and triturated with ether to give trans-4-(3-carbethoxypropylamino)-6-cyano-2,2-dimethyl-2H-benzo[b]pyran-3-ol hydrochloride (138 mg) of m.p. 198°–200°.

NMR (CD$_3$OD):

1.23 (s, 3H) overlapped with;
1.26 (t, J=8, 8 3H);
1.58 (s, 3H);
2.19 (m, 2H);
2.53 (m, 2H);
2.85–3.45 (irreg. m, 2H);
4.02 (d, J=10, 1H) overlapped with 4.16 (q, J=8, 8, 8 2H) and 3.75–4.65 (m, 3H, exchangeable);
4.53 (3, J=10, 1H);
7.00 (d, J=9, 1H);
7.60 (q, J=9, 2, 1H);
8.15 (d, J=2, 1H);

Analysis calculated for C$_{18}$H$_{25}$N$_2$O$_4$: C, 58.61; H, 6.83; N, 7.59%. Found: C, 58.55; H, 6.80; N, 7.29%.

The remainder of the ester fraction was heated under reflux in xylene (50 ml) for 7.25 hours. The solution was cooled and filtration gave 6-cyano-3,4-dihydro-2,2-dimethyl-trans-4-(2-oxo-1-pyrrolidinyl)-2H-benzo[b]-pyran-3-ol (425 mg) as crystals of m.p. 226° having an identical NMR spectrum and t.l.c. characteristics as the compound of Description 6.

DESCRIPTION 8

6-Cyano-3,4-dihydro-2,2-dimethyl-trans-4-(2-oxo-1-pyrrolidinyl)-2H-benzo[b]pyran-3-ol 6-Cyano-3,4-dihydro-2,2-dimethyl-trans-4-(1-keto-4-chlorobutylamino)-2H-benzo[b]pyran-3-ol (0.76 g), as obtained in Description 3, in dry tetrahydrofuran (10 ml) was added to a suspension of sodium hydride (0.15 g) in tetrahydrofuran (20 ml) and the reaction stirred under nitrogen for 3 hours. Addition of water and extraction via ethyl acetate gave 540 mg of the title compound having an identical NMR spectrum and tlc characteristics as the compound of Description 6.

DESCRIPTION 9

6-Cyano-3,4-dihydro-2,2-dimethyl-trans-4-(2-oxo-1-pyrrolidinyl)-2H-benzo[b]pyran-3-ol A solution of 6-cyano-3,4-dimethyl-trans-3-bromo-4-hydroxy-2H-benzo[b]pyran (4 g, 14.2 mM) in dimethylsulphoxide (20 ml) was stirred and sodium hydride (60% dispersion in oil, 0.6 g, 15 mM) added. The suspension was stirred for 1 hour when a solution of 6-cyano-3,4-dihydro-2,2-dimethyl-3,4-epoxy-2H-benzo[b]pyran resulted. 2-Pyrrolidone (1.8 g, 21 mM) and further sodium hydride (0.8 g, 21 mM) were introduced and the mixture stirred at room temperature for an additional 16 hours. Water (40 ml) was slowly added to the mixture to induce crystallisation of the product after which it was cooled in ice and filtered under suction. Crystallisation from ethanol (20 ml) gave the title compound as a cream coloured solid in 60% yield. Recrystallisation from ethyl acetate afforded the pure product as needles, m.p. 226.5°–227.5° having an nmr spectrum and t.l.c. characteristics identical to those of the compound of Description 6.

DESCRIPTION 10

6-Cyano-3,4-dihydro-2,2-dimethyl-trans-4-(2-oxo-1-pyrrolidinyl)-2H-benzo[b]pyran-3-ol 6-Cyano-3,4-dihydro-2,2-dimethyl-trans-4-(2-hydroxy-1-pyrrolidinyl)-2H-benzo[b]pyran-3-ol (5 mg), as obtained in Description 5, dissolved in methanol-water (1 ml) was treated with an excess of sodium periodate with stirring during 15 hours at room temperature. Evaporation of solvents and extraction by ethyl acetate gave material having identical thin layer characteristics when applied to silica gel plates developed in either chloroform-methanol (15:1) or heptane-ethyl acetate-triethylamine and infra red spectrum on the compound of Description 6.

DESCRIPTION 11

6-Cyano-3,4-dihydro-2,2-dimethyl-trans-4-(2-oxo-1-piperidinyl)-2H-benzo[b]pyran-3-ol 6-Cyano-3,4-dihydro-2,2-dimethyl-3,4-epoxy-2H-benzo[b]pyran and 2-piperidone were stirred in dimethyl sulphoxide under nitrogen at room temperature. Sodium hydride (81% dispersion in mineral oil) was added during 5 mins. and the reaction stirred for a further 6 hours. Addition of water, extraction with ethyl acetate, drying of the organic phase with magnesium sulpate, filtration, evaporation and recrystallisation from ethyl acetate gave 6-cyano-3,4-dihydro-2,2-dimethyl-trans-4-(2-oxo-1-piperidinyl)-2H-benzo[b]pyran-3-ol was prepared, as crystals of m.p. 155° C.

IR (KBr disc) 3480, 2212, 1612 cm$^{-1}$;
NMR (CDCl$_3$ soln):
1.25 (3H, s)
1.50 (3H, s)
1.63–2.10 (4H, m)
2.36–2.76 (2H, m)
3.72 (1H, d, J=10 Hz)
3.90–4.20 (1H, exchangeable, m)
5.72 (1H, d, J=10 Hz)
6.76 (1H, d, J=8 Hz)
7.17 (1H, m, narrow)
7.42 (1H, q, J=8, 2 Hz).

DESCRIPTION 12

6-Chloro-3,4-dihydro-2,2-dimethyl-trans-3-bromo-4-hydroxy-2H-benzo[b]pyran

The title compound was prepared analogously to the preparation of the 3-bromo-4-hydroxy compound of Description 1 giving a crude crystalline solid.
NMR (CDCl$_3$):
1.35 (3H, s),
1.53 (3H, s),
3.22 (1H, m),
4.00 (1H, d, J=9 Hz),
4.77 (1H, d, J=9 Hz),
6.51 (1H, d, J=8 Hz),
7.03 (1H, q, J=8.2 Hz),
7.30 (1H, narrow m).

DESCRIPTION 13

6-Chloro-3,4-dihydro-2,2-dimethyl-3,4-epoxy-2H-benzo[b]pyran

The crude crystalline solid (10.27 g) of Description 12 was dissolved in dimethyl sulphoxide (50 ml) and treated with sodium hydride (1.06 g, 80% dispersion on oil) over a period of an hour. The resulting material was used as such immediately in Description 13.

DESCRIPTION 14

6-Chloro-3,4-dihydro-2,2-dimethyl-trans-4-(2-oxo-1-pyrrolidinyl)-2H-benzo[b]pyran-3-ol 2-Pyrrolidone (4.5 g) and sodium hydride (1.59 g) were added to the material of Description 12, and the mixture stirred for 20 hours. Cautious addition of water and filtration of the resulting solid, followed by two crystallisations from ethyl acetate gave the title compound, m.p. 202°–203°.

DESCRIPTION 15

6-Acetyl-3,4-dihydro-2,2-dimethyl-trans-4-(2-oxo-1-pyrrolidinyl)-2H-benzo[b]pyran-3-ol 6-Acetyl-3,4-dihydro-2,2-dimethyl-3,4-epoxy-2H-benzo[b]pyran (0.33 g, prepared as described in Example 1 of U.K. Pat. No. 1,511,187), and 2-pyrrolidone (0.15 g), were stirred in dimethylsulphoxide (25 ml) under nitrogen at room temperature. Sodium hydride (0.05 g, 80%) was added during 2 mins and the reaction stirred for a further 22 hours. Addition of water, extraction with ethyl acetate, drying of the organic layer with magnesium sulphate, filtration, evaporation and recrystallisation from ethyl acetate gave the title compound (0.04 g) of m.p. 218°–219°.
NMR (CDCl$_3$:
1.32 (3H, s)

1.55 (3H, s)
1.85–2.25 (2H, m)
2.55 (3H, s) overlapped by
2.45–2.75 (2H, m)
2.80–3.45 (3H, m)
3.75 (1H, d, J=10 Hz)
5.36 (1H, d, J=10 Hz)
6.96 (1H, d, J=8 Hz)
7.63 (1H, narrow m)
7.83 (1H, q, J=8, 2 Hz).

EXAMPLE 1

6-Cyano-3,4-dihydro-2,2-dimethyl-trans-4-(2-thiaoxo-1-pyrrolidinyl)-2H-benzo[b]pyran-3-ol

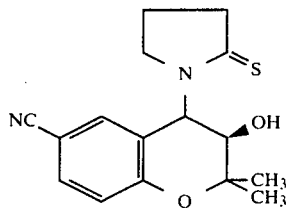

6-Cyano-3,4-dihydro-2,2-dimethyl-trans-4-N-(2-oxo-1-pyrrolidinyl)-2H-benzo[b]pyran-3-ol (500 mg), and Lawesson's reagent (354 mg, see B. S. Pedersen, S. Scheibye, N. H. Nilsson and S. -O. Lawesson, *Bull. Soc. Chim. Belg.*, 87, 223 (1978) were heated under reflux in dry toluene (100 ml) for 1 hr. in an atmosphere of nitrogen. The reaction was cooled and the solvent evaporated to give a yellow foam which was chromtographed on 40 g silica gel. Elution with chloroform and recrystallisation from benzene gave the title compound as pale yellow crystals (115 mg) of m.p. 175°–177° C.

Nmr (CDCl₃)
1.36 (s, 3H)
1.56 (s, 3H)
1.18 (m, 2H)
2.68 (broad m, 1H)
3.07–3.73 (m, 4H)
3.90 (d, J=10, 1H)
6.47 (d, J=10, 1H)
6.95 (d, J=8, 1H)
7.24 (narrow m, 1H)
7.53 (irreg q,, J=8, 2, 1H)
IR (KBr disc) 3300, 2220, 1160 cm⁻¹.

Mass spectrum (electron impact) $C_{16}H_{18}N_2OS$ requires M⁺ at M/z 302.1089 Found 302.1086.

EXAMPLE 2

6-Cyano-3,4-dihydro-2,2-dimethyl-trans-4-(2-thiaoxopiperidinyl)-2H-benzo[b]pyran-3-ol

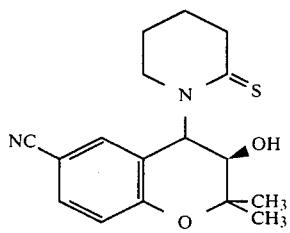

The title compound is prepared using Lawesson's reagent on 6-cyano-3,4-dihydro-2,2-dimethyl-trans-4-(2-oxo-1-piperidinyl)-2H-benzo[b]pyran-3-ol (Description 11).

EXAMPLE 3

6-Chloro-3,4-dihydro-2,2-dimethyl-trans-4-(2-thiaoxo-1-pyrrolidinyl)-2H-benzo[b]pyran-3-ol

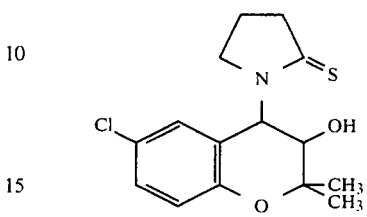

The title compound is prepared using Lawessons's reagent on 6-chloro-3-4-dihydro-2,2-dimethyl-trans-4-(2-oxo-1-pyrrolidinyl)-2H-benzo[b]pyran-3-ol (Description 14).

EXAMPLE 4

6-Acetyl-3,4-dihydro-2,2-dimethyl-trans-4-(2-thiaoxo-1-pyrrolidinyl)-2H-benzo[b]pyran-3-ol

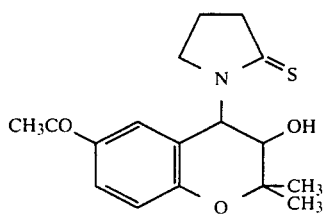

The title compound is prepared using Lawesson's reagent on a protected 6-acetyl-3,4-dihydro-2,2-dimethyl-trans-4-(2-oxo-1-pyrrolidinyl)-2H-benzo[b]pyran-3-ol (Description 15), followed by removal of the protecting group.

EXAMPLE 5

6-Nitro-3,4-dihydro-2,2-dimethyl-trans-4-(2-thiaoxo-1-pyrrolidinyl)-2H-benzo[b]pyran-3-ol

EXAMPLE 6

6-Nitro-3,4-dihydro-2,2-dimethyl-trans-4-(2-thiaoxo-1-piperidinyl)-2H-benzo[b]pyran-3-ol

EXAMPLE 7

6-Acetyl-3,4-dihydro-2,2-dimethyl-trans-4-(2-thiaoxo-1-piperidinyl)-2H-benzo[b]pyran-3-ol Examples 5, 6 and 7 were prepared analogously to Example 1, from analogous intermediates. (The intermediates are prepared analogously to Descriptions 2 to 11).

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses Prior to all measurements rats were placed in a heated environment (33.5±0.5° C.) before transfer to a restraining cage. Each determination of blood pressure was the mean of at least 6 readings. Spontaneously hypertensive rates (ages 12-18 weeks) with systolic blood pressures >170 mmHg were considered hypertensive.

| Compound of Example 1 | Time Post Dose Hours | % Change in Systolic Blood Blood | % Change in Heart Rate |
|---|---|---|---|
| 6 rats | 1 | −39 ± 6 | −6 ± 2 |
|  | 2 | −25 ± 7 | 0 ± 1 |
| Dose 0.3 mg/kg | 4 | −15 ± 4* | −1 ± 1 |
|  | 6 | −15 ± 5* | −3 ± 4 |
| Initial Blood Pressure 231 ± 8 mmHg |  |  |  |
| Initial Heart rate 479 ± 10 beats/min |  |  |  |

*1 rat had no measurable pulse.

TOXICITY

No toxic effects were observed on the above test.

We claim:

1. A compound of formula (I):

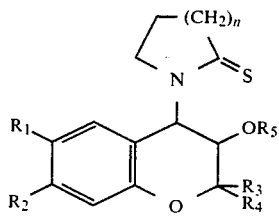

wherein:

either one of $R_1$ and $R_2$ is hydrogen and the other is $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto-$C_{2-7}$ alkyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl groups or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

$R_5$ is hydrogen, $C_{1-3}$ alkyl or $C_{1-8}$ acyl;

n is 1 or 2; the thiolactam group being trans to the OR$_5$ group; or, when one of $R_1$ and $R_2$ is an amino or an amino-containing group capable of forming an acid addition salt, a pharmaceutically acceptable salt thereof.

2. A compound according to claim 1, wherein one of $R_1$ and $R_2$ is hydrogen and the other is $C_{1-6}$ alkylcarbonyl, $C_{1-6}$ alkoxycarbonyl, $C_{1-6}$ alkylcarbonyloxy, nitro or cyano.

3. A compound according to claim 1, wherein one of $R_1$ and $R_2$ is hydrogen and the other is nitro, cyano or acetyl.

4. A compound according claim 1, wherein $R_2$ is hydrogen.

5. A compound according to claim 1, wherein $R_5$ is hydrogen.

6. A compound according to claim 1 which is
6-cyano-3,4-dihydro-2,2-dimethyl-trans-4-N-(2-thiaoxo-1-pyrrolidinyl)-2H-benzo[b]pyran-3-ol;
6-acetyl-3,4-dihydro-2,2-dimethyl-trans-4-N-(2-thiaoxopyrrolidinyl)-2H-benzo[b]pyran-3-ol;
6-chloro-3,4-dihydro-2,2-dimethyl-trans-4-N-(2-thiaoxopyrrolidinyl)-2H-benzo[b]pyran-3-ol;
6-cyano-3,4-dihydro-2,2-dimethyl-trans-4-N-(2-thiaoxopiperidinyl)-2H-benzo[b]pyran-3-ol;
6-nitro-3,4-dihydro-2,2-dimethyl-trans-4-N-(2-thiaoxopyrrolidinyl)-2H-benzo[b]pyran-3-ol; or
6-nitro-3,4-dihydro-2,2-dimethyl-trans-4-N-(2-thiaoxopiperidinyl)-2H-benzo[b]pyran-3-ol.

7. A compound according to claim 1 which is 6-cyano-3,4-dihydro-2,2-dimethyl-trans-4-N-(2-thiaoxopyrrolidinyl)-2H-benzo[b]pyran-3-ol.

8. An anti-hypertensive pharmaceutical composition which comprises an anti-hypertensive effective amount of a compound according to claim 1 of formula (I) or a pharmaceutically acceptable salt thereof and a pharmaceutically acceptable carrier.

9. A method of prophylaxis or treatment of hypertension in mammals including man, which comprises administering to the suffering mammal an anti-hypertensive effective amount of a compound according to claim 1 of formula (I) or a pharmaceutically acceptable salt thereof.

* * * * *